United States Patent [19]
Puckett et al.

[11] Patent Number: 5,068,347
[45] Date of Patent: Nov. 26, 1991

[54] PROCESS FOR THE PREPARATION OF 3-MERCAPTO-5-AMINO-(1H)-1,2,4-TRIAZOLE

[75] Inventors: Wallace E. Puckett, Memphis, Tenn.; R. Garth Pews, Midland, Mich.

[73] Assignee: DowElanco, Indianapolis, Ind.

[21] Appl. No.: 124,132

[22] Filed: Nov. 23, 1987

[51] Int. Cl.$^5$ .......................................... C07D 249/14
[52] U.S. Cl. ................................................. 548/263.8
[58] Field of Search ........................................ 548/263

[56] References Cited
U.S. PATENT DOCUMENTS
4,259,502  3/1981  Krüger ................................. 548/255

OTHER PUBLICATIONS
Y. Rao, *Indian J. Chem.;* 6 287–293 (1968) "Isomeric Changes Involving Amidino & Thioamidino Systems".
A. Sitte et al., *Monatsch,* 106, 1291–1292 (1975) "Umwandlung von 1,3,4 Thiadiazolinenin 1,2,4 Triazole".

*Primary Examiner*—Allen J. Robinson
*Assistant Examiner*—Peter G. O'Sullivan
*Attorney, Agent, or Firm*—Craig E. Mixan; Ronald G. Brookens

[57] ABSTRACT

3-Mercapto-5-amino-(1H)-1,2,4-triazole is prepared by the rearrangement of 2,5-diamino-1,3,4-thiadiazole. The rearrangement proceeds in high yields under aqueous alkaline conditions.

3 Claims, No Drawings

PROCESS FOR THE PREPARATION OF 3-MERCAPTO-5-AMINO-(1H)-1,2,4-TRIAZOLE

BACKGROUND OF THE INVENTION

3-Mercapto-5-amino-(1H)-1,2,4-triazole is known to be useful as a component of heat-developable, image-pattern, recording compositions as demonstrated by Hirabayashi et al. in U.S. Pat. No. 4,543,309. It has also found use in preparing stabilizers for photographic emulsions as taught by Merrifield et al. in British Patent No. 1,232,838. More recently, 3-mercapto-5-amino-(1H)-1,2,4-triazole has been disclosed as an intermediate for the manufacture of herbicidal compounds in European Patent Application No. 142,152.

Prior art methods of preparing 3-mercapto-5-amino-(1H)-1,2,4-triazole have generally involved condensation and/or cyclization reactions. For example, British Patent No. 1,232,838 describes the condensation of a salt of aminoguanidine with carbon disulfide to produce guanidinodithiocarbamic acid and the subsequent ring closure of this intermediate with boiling alkali. U.S. Pat. No. 4,543,309 describes the cyclization of N-guanidinothiourea hydrochloride with refluxing aqueous caustic Godfrey et al., in J. Chem. Soc., 3437 (1960), describe the condensation of isothiocyanic esters with aminoguanidine to form (amino)amidinothioureas followed by the acidic hydrolysis and cyclization of the hydrazones thereof. Polish Patent No. 126,718 describes the cyclization of $H_2NC(S)NHNHC(S)NH_2$. Typical yields for the above preparations of 3-mercapto-5-amino-(1H)-1,2,4-triazole range from about 40 to about 80 percent.

SUMMARY OF THE INVENTION

The present invention is directed to a process for the preparation of 3-mercapto-5-amino-(1H)-1,2,4-triazole by the rearrangement of 2,5-diamino-1,3,4-thiadiazole. The present process, which provides the desired product in nearly quantitative yield, comprises contacting 2,5-diamino-1,3,4-thiadiazole or a salt thereof with a base in a suitable solvent. The desired product can be isolated by neutralizing the reaction mixture and collecting the product by filtration.

DETAILED DESCRIPTION OF THE INVENTION

It has been discovered that 3-mercapto-5-amino-(1H)-1,2,4-triazole can be prepared in high yield by the rearrangement of 2,5-diamino-1,3,4-thiadiazole. The conversion can be achieved by contacting the 2,5-diamino-1,3,4-thiadiazole or a salt thereof with a base in a suitable solvent.

The starting material, 2,5-diamino-1,3,4-thiadiazole is known in the art, and its preparation has been disclosed, for example, by Fromm in Ann. Chem, 433, 1 (1923) and by Gehlen et al. in Ann. Chem., 685, 176 (1965). The starting material can be used as the free base or in the salt form. Suitable salts include those formed by contacting the free base with mineral acids. Hydrohalides are the preferred salts. For example, it is convenient to employ the hydrobromide or the hydrochloride salts of 2,5-diamino-1,3,4-thiadiazole which can be directly prepared from thiosemicarbazide and cyanogen bromide or cyanogen chloride respectively.

Inorganic bases are typically employed in the present invention, but organic amine bases are also suitable. The preferred bases include the alkali metal and alkaline earth hydroxides and carbonates, in particular, sodium hydroxide or potassium hydroxide. The rearrangement reacton is catalytic in base but preferably one equivalent of base per mole of 2,5-diamino-1,3,4-thiadiazole is employed. If, for example, a hydrohalide salt is used as the starting material, an additional equivalent of base is required to neutralize the salt and provide the starting material in the form of the free base.

Polar protic solvents and mixtures thereof are suitable solvents for the present invention. For convenience, either water alone or aqueous alcoholic combinations are preferred.

The reaction is routinely conducted at elevated temperatures. Temperatures in the range of about 40° C. to reflux are conveniently employed. Temperatures in the range from about 60° C. to about 100° C. are preferred.

The reaction can be performed at reduced or elevated pressures, but reaction at atmospheric pressure is usually most convenient.

After completion of the reaction, the product can be isolated by standard procedures. In general, it is most convenient to cool and neutralize the reaction mixture and to collect the desired product by filtration.

The following examples are illustrative of the invention and are not intended as a limitation thereof.

Example 1

2,5-diamino-1,3,4-thiadiazole

Thiosemicarbazide (10 g: 0.11 mole) and cyanogen bromide (11.6 g; 0.11 mole) were stirred in 100 milliliters of water at 80° C. for two hours. The reaction mixture was cooled in ice to yield 17 g of 2,5-diamino-1-3-4-thiadiazole hydrobromide which was collected by filtration (two crops). mp 280°–284° C. The $^{13}C$ NMR in DMSO was consistent with the structure.

The mass spectrum of the free base (mp 210° C.) was similarly consistent with the structure.

Example 2

3-Mercapto-5-amino-(1H)-1,2,4-triazole 2,5-diamino-1,3,4-thiadiazole hydrobromide (1.96 g; 0.01 mole) was heated at 80° C. for two (2) hours with 0.8 g (0.02 mole) of NaOH in water. The reaction mixture was cooled and neutralized with mineral acid. 3-Mercapto-5-amino(1H)-1,2,4-triazole (1.1 g; 94.8%) was collected by filtration. mp $\geq$300° C. The $^{13}C$ NMR spectrum was consistent with the structure.

What is claimed is:

1. A process for the preparation of 3-mercapto-5-amino-(1H)-1,2,4-triazole which comprises contacting 2,5-diamino-1,3,4-thiadiazole or a salt thereof with a base in a suitable solvent.

2. The process according to claim 1 wherein an aqueous solvent is used.

3. The process according to claim 2 wherein the base is an inorganic compound selected from the group consisting of alkali metal hydroxides, alkaline earth hydroxides, alkali metal carbonates, and alkaline earth carbonates.